US00PP15214P3

(12) United States Plant Patent
Utecht

(10) Patent No.: US PP15,214 P2
(45) Date of Patent: Oct. 12, 2004

(54) ***GERANIUM* PLANT NAMED 'FISBLIPUR'**

(50) Latin Name: *Pelargonium peltatum*
Varietal Denomination: Fisblipur

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,535

(22) Filed: Nov. 19, 2003

(65) Prior Publication Data

US 2004/0123364 P1 Jun. 24, 2004

(30) Foreign Application Priority Data

Dec. 23, 2002 (CA) ..... 02-3398

(51) Int. Cl.[7] ..... A01H 5/00

(52) U.S. Cl. ..... Plt./332

(58) Field of Search ..... Plt./332

*Primary Examiner*—Kent Bell

(74) *Attorney, Agent, or Firm*—Foley & Lardner LLP

(57) ABSTRACT

A new and distinct cultivar of *geranium* plant named 'Fisblipur', particularly characterized by the combined features of purple, single-type flowers, large inflorescences, mid-season beginning of flowering, medium green foliage with distinct zonation, freely branching, and initially round and bushy, later long trailing plant habit.

1 Drawing Sheet

Genus and species of the plant claimed: Hybrid of *Pelargonium peltatum* L'Héritier.
Variety denomination: 'Fisblipur'.

BACKGROUND OF THE INVENTION

The present invention comprises a new and distinct cultivar of *geranium,* botanically known as *Pelargonium peltatum,* and hereinafter referred to by the cultivar named 'Fisblipur'.

'Fisblipur' is a product of a planned breeding program which had the objective of creating new ivy *geranium* cultivars with single-type flowers, zoned foliage, and relatively vigorous, but well-branched growth habit, in various flower colors.

'Fisblipur' originated from a hybridization made by the inventor, Angelika Utecht, in a controlled breeding program in Galdar, Gran Canaria, Spain, in 1998. The female parent was the commercial variety 'Fisbliz' (U.S. Plant Pat. No. 9,373), having white single-type flowers, medium green foliage with weak zonation, vigorous growth and long trailing plant habit. The male parent of 'Fisblipur' was the unpatented hybrid seedling no. 95/810-1, characterized by red, semi-double flowers, foliage with relatively strong zonation, and about medium growth habit.

'Fisblipur' was selected as one flowering plant within the progeny of the stated cross by Angelika Utecht in 1999 in a controlled environment in Moncarapacho, Portugal.

The first act of asexual reproduction of 'Fisblipur' was accomplished when vegetative cuttings were taken from the initial selection in the fall of 1999 in a controlled environment in Moncarapacho, Portugal, Spain, by, or under the supervision of, Angelika Utecht.

Horticultural examination of plants grown from cuttings of the plant initiated in May 2000 in Hillscheid, Federal Republic of Germany, and continuing thereafter, has demonstrated that the combination of characteristics as herein disclosed for 'Fisblipur' are firmly fixed and are retained through successive generations of asexual reproduction.

'Fisblipur' has not been observed under all possible environmental conditions. The phenotype may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fisblipur' in combination distinguish this *geranium* as a new and distinct cultivar:

1. Brilliant, purple colored, single-type flowers;
2. Big inflorescences with relatively many, large flowers;
3. Deep green foliage with distinct zonation;
4. Vigorous growth, trailing, but very well-branched plant habit; and
5. About medium (mid season) spring flowering response.

Of the many commercial cultivars known to the present inventor, none is very close in comparison.

BRIEF DESCRIPTION OF THE DRAWINGS

The accompanying photographic drawing shows typical flower and foliage characteristics of 'Fisblipur' with colors being as true as possible with an illustration of this type. The photographic drawing on the top of the sheet shows a 'Fisblipur' plant in a hanging basket and the photographic drawing on the bottom of the sheet shows a branch end of 'Fisblipur' with leaves, buds, and inflorescences.

DETAILED BOTANICAL DESCRIPTION

In the following description color references are made to The Royal Horticultural Society Colour Chart. The color values were determined indoors from plants growing in a green-house in May 2003, in Hillscheid, Germany. The measurements were taken in Hillscheid, Germany, in mid May 2003, 15 weeks after planting of rooted cuttings. The plants were growing in 14 cm pots; they had been pinched once.

INFLORESCENCE

Umbel:

*Shape.*—Irregular to nearly semi-spherical.
*Average diameter.*—131 mm.
*Average depth.*—65–70 mm.
*Peduncle length.*—205 mm.
*Peduncle color.*—Light green, RHS 143 C.
*Pedicel.*—46 mm in length, occasionally with a spur near the base of the flower.
*Pedicel color.*—Light green, RHS 144 B, usually no anthocyanin (no brownish hue).
*Number of flowers per umbel.*—About 12–16.

Corolla:

*Average diameter.*—56 mm.
*Form.*—Single-type.
*Shape.*—Round outline, with the upper petals about the same size as the lower petals, petals not overlapping.
*Number of petals.*—Mostly 5, occasionally 6–7.
*Number of petaloids.*—None.
*Shape of petals.*—Obovate, base acute or attenuate, upper end is rounded, margin is entire or slightly crenate.
*Size of petals.*—Upper petals: 29–30 mm long, 20–21 mm wide Lower petals: 24–25 mm long, 19–21 mm wide.
*Color (general tonality from a distance of three meters)*.—Brilliant purple, uniform.
*Color of upper petals.*—Closest to RHS N66 A.
*Markings of upper petals.*—2 dark purple veins, RHS N77 A.
*Color of lower petals.*—Between RHS N66 A and RHS N66 B, turning more bluish, closest to RHS 74 B.
*Markings of lower petals.*—None.
*Color of lower surface of petals.*—Approximately RHS 61 C.
*Color of sepals.*—Outer, visible lower surface: light green, RHS 143 C; inner surface: light green, RHS 144 A.
*Number of sepals.*—5.
*Shape of sepals.*—Linear to lanceolate, acute tip, truncate base, surface with weak pubescence, margin entire.
*Size of sepals.*—12–13 mm long, 5 mm wide for the largest upper sepal, 3 mm in width for the other sepals.

Bud: (just prior to petals unfolding)

*Shape.*—Narrow, elliptical.
*Color of sepals.*—Light green, RHS 143 C.
*Color of petals.*—RHS 61 B.
*Length.*—21 mm.
*Width.*—7 mm.

REPRODUCTIVE ORGANS

*Androecium.*—7 fertile anthers, plenty pollen, yellow-orange, RHS 28 A, lower side of anthers blackish, RHS 187 A, filaments white, RHS 155 D, to light-pink, RHS 52 D.
*Gynoecium.*—One pistil, whitish style, RHS 155 D to 65 D, stigma 5–6-lobed stigma, dark purple, RHS 59 B.
*Fertility/seed set.*—Relatively little for a single-type flowered variety, mainly from late summer to fall.
*Fruit.*—Oblong, about 6 mm wide, rostrum (beak) 38–42 mm long.
*Seed.*—Oblong, 4–5 mm long, brown, RHS 177 B.

Spring flowering response period: In Hillscheid, Germany, in 2001 plants had on average 0.4 flowers opened 12 weeks after planting of rooted cuttings (pinched plants).

Outdoor flower production: Continuously and moderately rich flowering, the flower count in 2003 in Hillscheid, Germany, indicated about 3 inflorescence per plant in mid May.

Durability: Good stability of flower color, little fading, good rain resistance.

Lastingness of the individual flower: About 7 days at 18° C.

Fragrance: None.

PLANT

Foliage:

*Shape.*—Ivy-shaped, with cordate base, with the gap between the lowest lobes closed to overlapping, apex rounded with weak to moderate lobes.
*Margin.*—Entire, slightly wavy.
*Texture.*—Upper surface smooth, dull or slightly glossy.
*Size of leaf.*—82 mm wide, about 50 mm long.
*Color of upper surface.*—Medium green, closest to RHS 137 C to 137 D.
*Color of zonation.*—Brown, closest to RHS 166 A, distinctness: medium to strong.
*Color of lower surface.*—RHS 143 C.
*Petiole.*—85 mm long, 2–3 mm diameter, light green in color, closest to RHS 143 B.

General appearance and form:

*Stem color.*—Light green, RHS 143 B.
*Internode length.*—45–70 mm.
*Branching pattern.*—13 branches on average.
*Size of plants.*—28.5 cm (15 week-old plants, as described), and 100 cm (30 week-old plants, around September 1), measured from the top of the soil (base of the main stem) to the tips of the branches, without inflorescences.

I claim:

1. A new and distinct cultivar of *geranium* plant named 'Fisblipur', as described and illustrated herein.

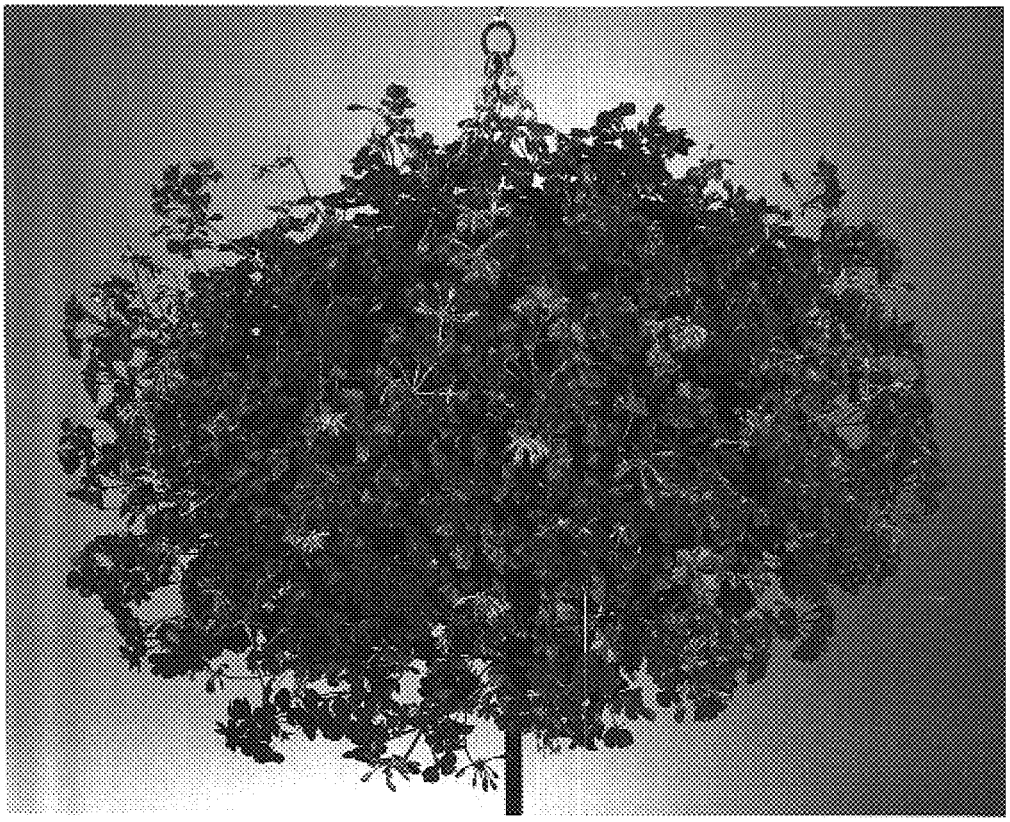
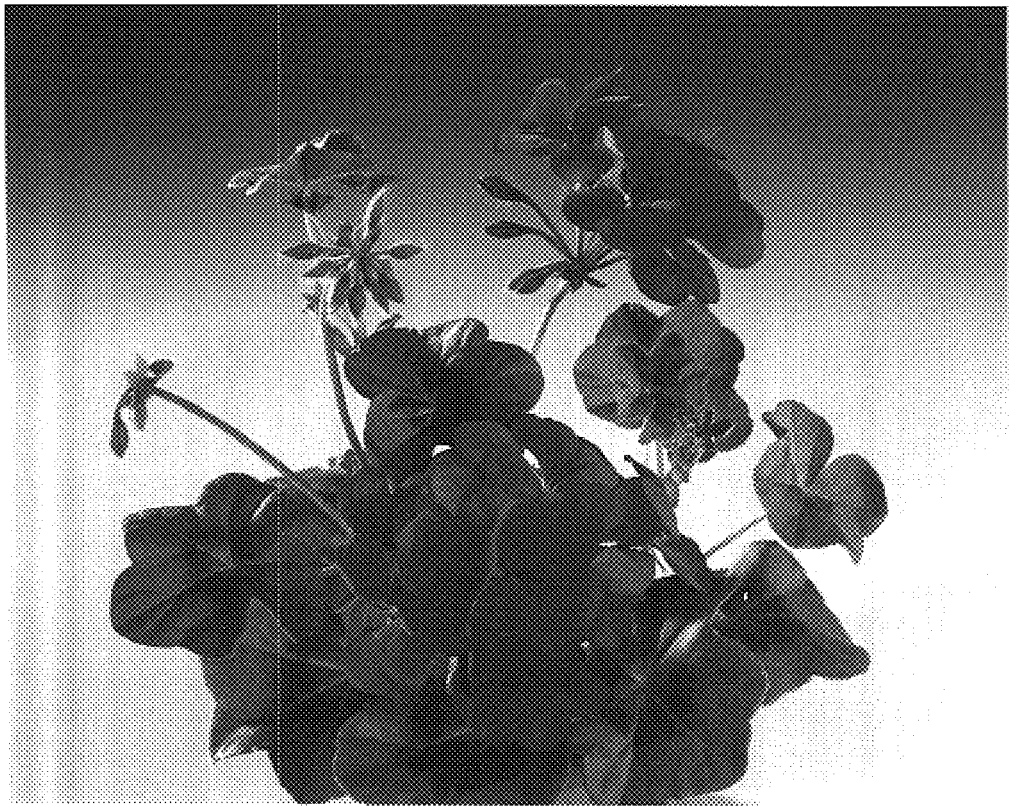

* * * * *